United States Patent
Williams et al.

(10) Patent No.: US 12,059,366 B2
(45) Date of Patent: Aug. 13, 2024

(54) JOINT ORTHOSIS WITH RESILIENTLY DEFORMABLE HINGE

(71) Applicant: University of Derby, Derby (GB)

(72) Inventors: Gavin Williams, Derby (GB); Paul Wood, Derby (GB); Jennifer Clementson, Derby (GB)

(73) Assignee: University of Derby, Derby (GB)

( * ) Notice: Subject to any disclaimer, the term of this patent is extended or adjusted under 35 U.S.C. 154(b) by 549 days.

(21) Appl. No.: 17/290,318

(22) PCT Filed: Oct. 31, 2019

(86) PCT No.: PCT/GB2019/053097
§ 371 (c)(1),
(2) Date: Apr. 30, 2021

(87) PCT Pub. No.: WO2020/089642
PCT Pub. Date: May 7, 2020

(65) Prior Publication Data
US 2021/0378855 A1 Dec. 9, 2021

(30) Foreign Application Priority Data
Nov. 2, 2018 (GB) ..................... 1817926

(51) Int. Cl.
*A61F 5/01* (2006.01)
*B33Y 50/00* (2015.01)
*B33Y 80/00* (2015.01)

(52) U.S. Cl.
CPC .... *A61F 5/0127* (2013.01); *A61F 2005/0165* (2013.01); *B33Y 50/00* (2014.12); *B33Y 80/00* (2014.12)

(58) Field of Classification Search
CPC .... A61F 5/0127; A61F 5/0102; A61F 5/0111; A61F 5/14; A61F 5/0113; A61F 5/0585; A61F 5/019; A61H 2201/1676
See application file for complete search history.

(56) References Cited

U.S. PATENT DOCUMENTS 4,962,760 A * 10/1990 Jones .................... A61F 5/0127
36/31
9,707,118 B1   7/2017 Meyer et al.
(Continued)

FOREIGN PATENT DOCUMENTS

EP     2417944 A1   8/2010
JP     H11128258 A  5/1999
(Continued)

OTHER PUBLICATIONS

"International Search Report and Written Opinion for PCT Patent Application No. PCT/GB2019/053097", Mailed Date: Jan. 21, 2020, 13 Pages.
(Continued)

*Primary Examiner* — Ophelia A Hawthorne
(74) *Attorney, Agent, or Firm* — Calfee, Halter & Griswold LLP

(57) ABSTRACT

An joint orthosis such as an ankle foot orthosis for controlling joint movement is disclosed, and a method of manufacture. The joint orthosis comprises: a hinge for controlling joint movement in at least one direction; wherein the hinge comprises at least one resiliently deformable portion, and wherein the resiliently deformable portion is configured to resiliently deform in response to at least the joint movement in the at least one direction, to resist further joint movement in the at least one direction.

20 Claims, 4 Drawing Sheets

(56) References Cited

U.S. PATENT DOCUMENTS

| | | | |
|---|---|---|---|
| 2004/0002672 A1 | 1/2004 | Carlson | |
| 2009/0069732 A1* | 3/2009 | Jackovitch | A61F 5/0127 602/23 |
| 2014/0066829 A1 | 3/2014 | Drillio | |
| 2014/0114223 A1* | 4/2014 | Ingimundarson | A61F 5/0111 602/16 |
| 2014/0180185 A1 | 6/2014 | Zachariasen | |
| 2015/0216703 A1* | 8/2015 | Madden | A61F 5/0127 602/7 |
| 2016/0022466 A1* | 1/2016 | Pedtke | A61F 5/0127 700/98 |
| 2016/0074203 A1 | 3/2016 | Hall | |
| 2016/0235158 A1 | 8/2016 | DesJardins et al. | |
| 2018/0177624 A1 | 6/2018 | Vlasic | |
| 2018/0228401 A1 | 8/2018 | Schwartz et al. | |

FOREIGN PATENT DOCUMENTS

| | | |
|---|---|---|
| JP | H11313862 A | 11/1999 |
| JP | 5561688 B2 | 7/2014 |
| JP | 2016049393 A | 4/2016 |
| WO | 02065942 A2 | 8/2002 |
| WO | 2016015011 A1 | 1/2016 |
| WO | 2017208256 A1 | 12/2017 |
| WO | 2020089642 A1 | 5/2020 |

OTHER PUBLICATIONS

"Search Report for UK Patent Application No. GB1817926.7", Mailed Date: Mar. 6, 2019, 2 Pages.

"Office Action for Great Britain Patent Application No. GB1817926.7", Mailed Date: Dec. 13, 2022, 4 pages.

"Office Action for Great Britain Patent Application No. 1817926.7", Mailed Date: Jun. 24, 2022, 3 pages.

1 Office Action in European Application No. 19798370.3, Mailed Date: May 2, 2024, 5 pages.

* cited by examiner

JOINT ORTHOSIS WITH RESILIENTLY DEFORMABLE HINGE

FIELD OF THE INVENTION

Embodiments of the present invention relate to a joint orthosis with a joint hinge. In particular, they relate to an ankle foot orthosis with a resiliently deformable hinge.

BACKGROUND TO THE INVENTION

Joint orthoses such as ankle foot orthoses are known. An ankle foot orthotic controls position and motion of an ankle, compensates for ankle weakness, or corrects deformities.

One ankle foot orthosis design is a hinge-less sleeve or wrap-around that can be worn like a sock. This design provides a lower level of ankle immobilization.

A hinge-type ankle foot orthotic design comprises rigid ankle-receiving and foot-receiving portions, coupled to each other by a distinct hinge. This provides a greater degree of immobilization. The hinge may comprise a rivet, and strengthening material to strengthen the area around the rivet. The hinge is bulky and can cause discomfort when the ankle foot orthotic is worn under a shoe. The hinge offers limited shock absorption and movement resistance which can cause discomfort.

BRIEF DESCRIPTION OF VARIOUS EMBODIMENTS OF THE INVENTION

According to various, but not necessarily all, embodiments of the invention there is provided an ankle foot orthosis for controlling joint movement, the ankle foot orthosis comprising: an ankle hinge for controlling ankle movement in at least one direction; wherein the ankle hinge comprises at least one resiliently deformable portion, and wherein the resiliently deformable portion is configured to resiliently deform in response to at least the ankle movement in the at least one direction, to resist further ankle movement in the at least one direction.

An advantage is a more comfortable ankle foot orthotic, such as when worn under a shoe and when walking.

In some examples, the at least one direction comprises dorsiflexion or plantarflexion, wherein the resiliently deformable portion is configured to resiliently stretch in response to the dorsiflexion or plantarflexion.

An advantage is more comfortable flexion control.

In some examples, the at least one direction comprises a plurality of directions, the plurality of directions selected from the group comprising: dorsiflexion; plantarflexion; inversion; eversion; abduction; or adduction.

An advantage is that limited ankle rotation about different axes is permitted, which is advantageous for some injuries.

In some examples, the resiliently deformable portion comprises material with a shore A hardness of less than 70.

An advantage is a more comfortable ankle foot orthotic to walk in.

In some examples, the resiliently deformable portion is on a heel side of the ankle foot orthosis, and a width of the resiliently deformable portion extends in a posterior direction and towards the sagittal plane of the ankle foot orthosis.

An advantage is that the same resiliently deformable portion can control ankle rotation about more than one axis.

In some examples, the width of the resiliently deformable portion is less than half of the maximum width of the ankle foot orthosis. In some examples, the resiliently deformable portion is a first resiliently deformable portion on one of the medial or lateral side of the ankle foot orthosis, the ankle hinge further comprising a second resiliently deformable portion on the other of the medial or lateral side.

An advantage is reduced stress of the resiliently deformable portion for some ankle rotations.

In some examples, the resiliently deformable portion has an average thickness of no more than approximately 8 mm.

An advantage is improved comfort when worn under a shoe.

In some examples, the ankle hinge enables movement of an ankle-receiving portion relative to a foot-receiving portion, wherein the ankle-receiving portion and the foot-receiving portion are rigid relative to the resiliently deformable portion.

In some examples, a lengthwise direction of the resiliently deformable portion spans from the foot-receiving portion to the ankle-receiving portion. In some examples, the at least one resiliently deformable portion is configured to support the weight of at least the ankle-receiving portion such that a gap is maintained between the ankle-receiving portion and the foot-receiving portion.

An advantage is that the ankle hinge can consist of resiliently deformable portion(s), with no intervening or additional hinge support.

In some examples, the ankle foot orthosis comprises means for enabling the ankle-receiving portion and/or the foot-receiving portion to be secured to the human body. In some examples, the means comprises a strap or a portion for securing a strap to the ankle-receiving portion.

An advantage is enabling improved support and reduced slippage.

In some examples, the resiliently deformable portion comprises a first material, and wherein the foot-receiving portion and/or the ankle-receiving portion comprises the same first material.

An advantage is enabling single material manufacture, which can facilitate single step manufacture. Little to no post-forming fabrication or assembly may be required.

In some examples, the ankle foot orthosis comprises an insole layer for providing cushioning to a patient's foot.

An advantage is a more comfortable ankle foot orthotic.

In some examples, the ankle foot orthosis comprises one or more apertures for enabling air circulation to a patient's skin.

An advantage is a more comfortable ankle foot orthotic to be worn for long periods.

In some examples, the ankle foot orthosis comprises a toe hinge for enabling toe flexion. In some examples, the toe hinge comprises one or more portions of reduced material thickness for enabling the toe flexion. In some examples, the hinge is formed by a plurality of the portions. In some examples, the one or more portions are provided by channels, depths of the channels defining the extent of the reduced material thickness. In some examples, the channels are dimensioned such that facing channel walls of the channels abut during toe flexion in a first toe flexion direction to inhibit further toe flexion in the first toe flexion direction.

An advantage is a more comfortable ankle foot orthotic for walking and for reducing toe muscle atrophy. An advantage of a reduced material thickness hinge is that the toe hinge can be formed integrally.

According to various, but not necessarily all, embodiments of the invention there is provided a method of manufacturing an ankle foot orthosis for controlling joint motion, the method comprising: providing an ankle hinge for controlling ankle movement in at least one direction; wherein the ankle hinge comprises at least one resiliently deformable portion, and wherein the resiliently deformable portion is configured to resiliently deform in response to at least the ankle movement in the at least one direction, to resist further ankle movement in the at least one direction.

In some examples, the method comprises providing an ankle-receiving portion and a foot-receiving portion, wherein the ankle-receiving portion and the foot-receiving portion are rigid relative to the resiliently deformable portion. In some examples, the resiliently deformable portion, the ankle-receiving portion, and/or the foot-receiving portion, are additively manufactured. In some examples, the resiliently deformable portion, the ankle-receiving portion, and/or the foot-receiving portion, are formed by a single step 3D print.

An advantage is enabling single step manufacture. 3D printing can be performed automatically from scanned images of patient's ankles and feet. Therefore, bespoke ankle foot orthotics can be created quickly.

According to various, but not necessarily all, embodiments of the invention there is provided an ankle foot orthosis obtained directly by means of the method. Evidence that a single step 3D print has been used may comprise an absence of post-forming assembly marks or joins. Evidence that a single step 3D print has been used may comprise use of a same material for the resiliently deformable portion and the ankle/foot-receiving portion.

Various, but not necessarily all, embodiments of the invention may be applied to a joint orthosis other than an ankle foot orthotic. Instead of an ankle hinge, a joint hinge is provided for the joint concerned. Instead of an ankle-receiving portion, a first body part receiving portion is provided. Instead of a foot-receiving portion, a second body part receiving portion is provided. Example applications include elbows, wrists, knees and hips. According to various, but not necessarily all, embodiments of the invention there is provided a joint orthosis for controlling joint movement, the joint orthosis comprising: a joint hinge for controlling joint movement in at least one direction; wherein the joint hinge comprises at least one resiliently deformable portion, and wherein the resiliently deformable portion is configured to resiliently deform in response to at least the joint movement in the at least one direction, to resist further joint movement in the at least one direction. The at least one direction may comprise flexion about a first axis, and optionally rotation about one or more other axes.

BRIEF DESCRIPTION OF THE DRAWINGS

For a better understanding of various examples of embodiments of the present invention reference will now be made by way of example only to the accompanying drawings in which.

DETAILED DESCRIPTION OF VARIOUS EMBODIMENTS OF THE INVENTION

The Figures illustrate an ankle foot orthosis 1 for controlling joint movement, the ankle foot orthosis 1 comprising: an ankle hinge 2 for controlling ankle movement in at least one direction; wherein the ankle hinge 2 comprises at least one resiliently deformable portion 3, and wherein the resiliently deformable portion 3 is configured to resiliently deform in response to at least the ankle movement in the at least one direction, to resist further ankle movement in the at least one direction.

Figure 1:
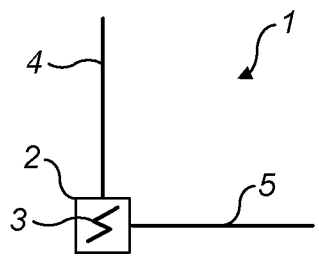
FIG. 1 illustrates an example of an ankle foot orthotic.

FIG. 1 schematically illustrates an example implementation of an ankle foot orthosis 1 according to various aspects of the present invention.

Figure 2:
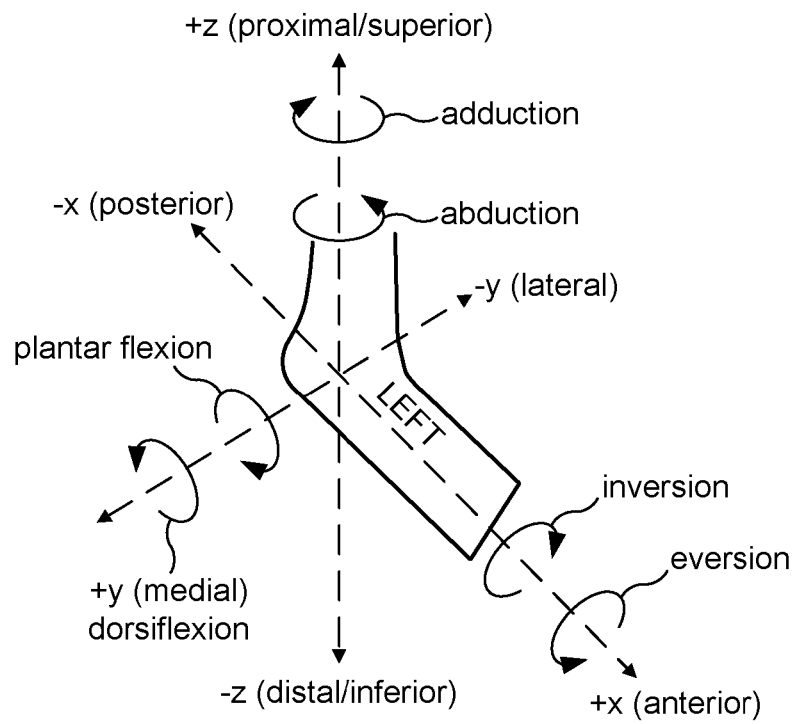
FIG. 2 illustrates and labels a coordinate system and ankle movement directions.

FIG. 2 illustrates standard anatomical terms of location and motion, applied to a left foot ankle foot orthosis 1. To briefly summarise FIG. 2 by analogy to a three dimensional Cartesian coordinate system, the +x direction (direction in which toe points) is anterior, the -x direction is posterior, the +y direction (towards right foot) is medial, the -y direction is lateral, the +z direction (upwards) is proximal (superior), and the -z direction is distal (inferior). From an observer at the origin looking along the respective axes, clockwise rotation about the +x-axis is eversion, while anticlockwise is inversion. Clockwise rotation about the +y-axis is dorsiflexion, while anticlockwise is plantarflexion. Clockwise rotation about the +z-axis is adduction, while anticlockwise is abduction. The sagittal plane is the x-z plane passing through the origin which is in the putative centre of the foot.

Referring to FIG. 1, the ankle foot orthosis 1 comprises the ankle hinge 2, the ankle-receiving portion 4 and the foot-receiving portion 5.

The ankle-receiving portion 4 is a plate-like structure configured to receive an ankle of a patient, which may be curved about the z-axis.

The ankle-receiving portion 4 may be sized to receive at least a portion of a lower leg of a patient, or a separate lower leg-receiving portion may be provided above the ankle-receiving portion 4.

If the ankle foot orthosis 1 is a knee ankle foot orthosis, the ankle-receiving portion 4 may further receive a knee, or an additional knee-receiving portion may be provided above the ankle-receiving portion 4.

Figure 4A:
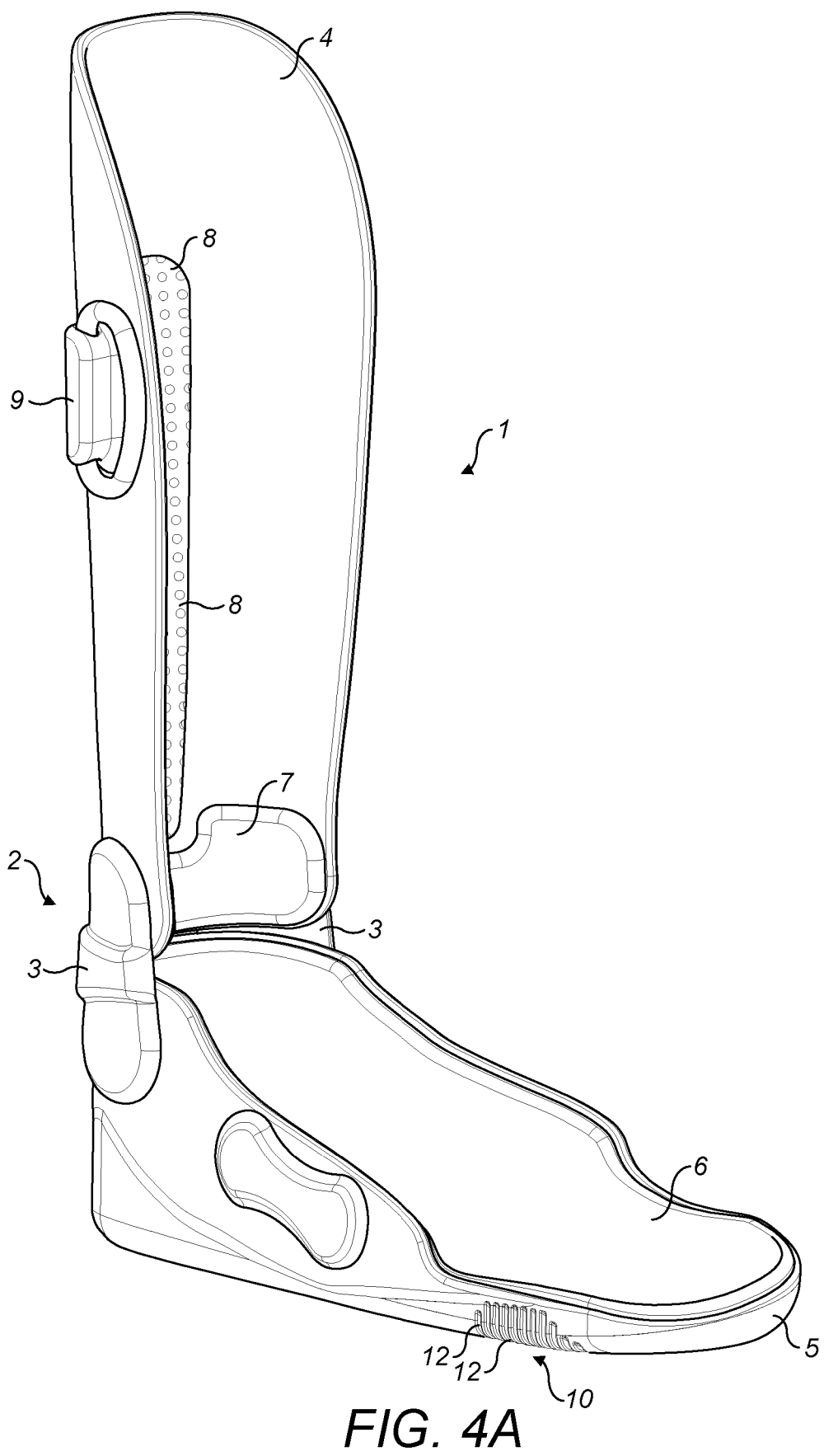
FIG. 4A illustrates an example of an ankle foot orthotic and FIG. 4B illustrates the ankle foot orthotic viewed from another angle.
Figure 4B:
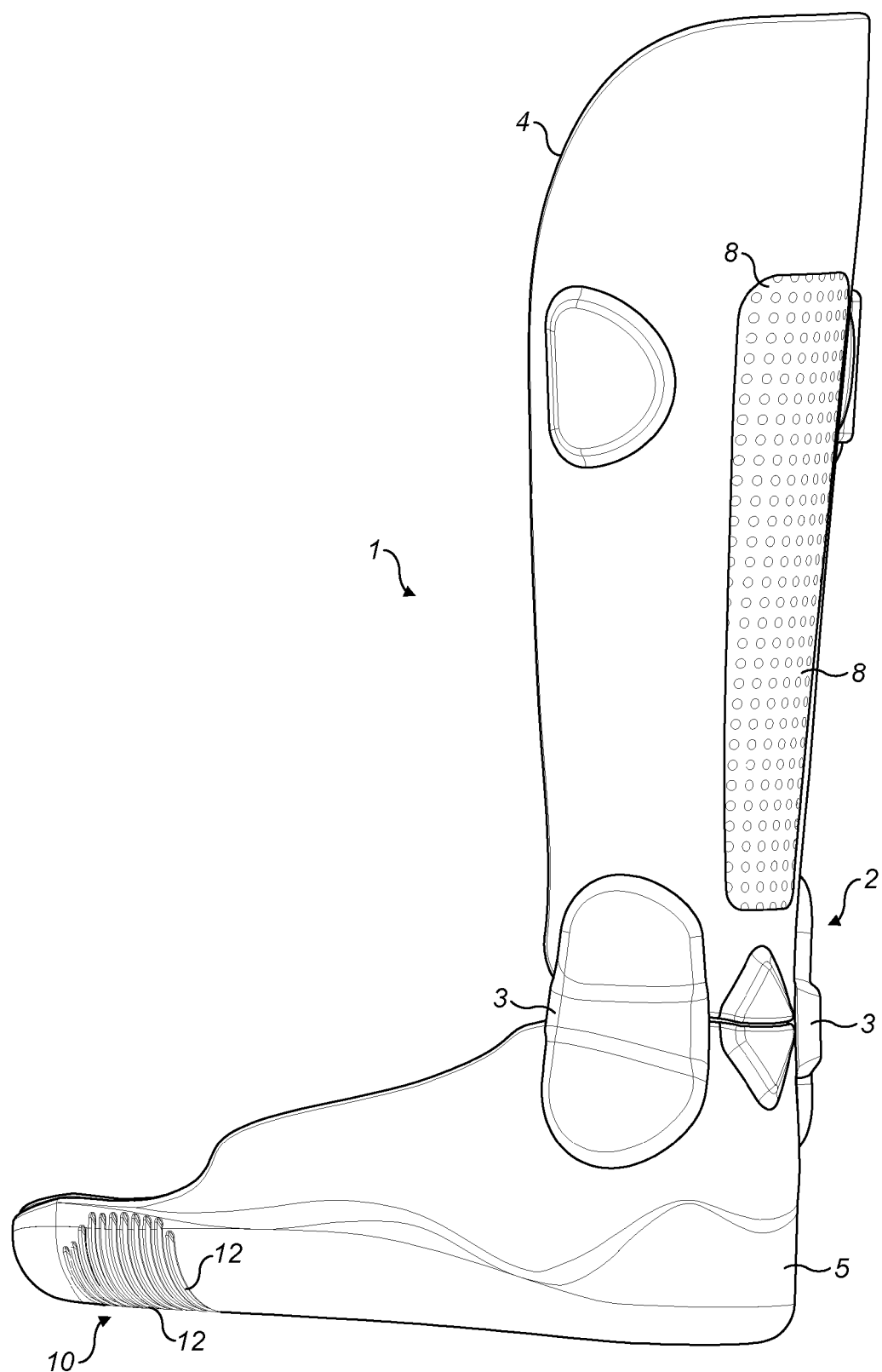

The ankle-receiving portion 4 may be shaped to follow the contours of the body part(s) of the patient to be inserted. See for example the ankle-receiving portion 4 as shown in FIGS. 4A-4B.

An interior surface of the ankle-receiving portion 4 may follow contours of an Achilles tendon region of a patient's lower leg, and optionally the calf region.

The ankle-receiving portion 4 may partially wrap around the patient's ankle, and optionally the calf region, by curvature about the z-axis.

The ankle-receiving portion 4 may not wrap around the ankle as far as the anterior side. The open space in the anterior side is to facilitate insertion of the patient's ankle into the ankle-receiving portion 4 from the anterior side.

In other examples, the ankle receiving portion may have any other shape or size to suit different medical needs.

The foot-receiving portion 5 is configured to receive and support a patient's foot.

The foot-receiving portion 5 comprises a sole. The sole may be sized to support a whole foot, including toes. Alternatively, the sole may be sized to support a part of a foot, for example the anterior end of the sole may be sized to be posterior of the patient's toes.

The foot-receiving portion 5 may comprise a medial side support, a lateral side support, a posterior end support, or a combination thereof. The side and end supports are upstanding relative to the sole. The sole, side and end supports define a cavity for the patient's foot, providing restraint against at least lateral, medial and posterior movement of the foot. The sole may continuously curve into the side and end supports. The curvature may follow the contours of the patient's foot.

In FIGS. 4A-4B, the foot-receiving portion 5 is open toed and open topped. This facilitates insertion of the patient's foot into the foot-receiving portion 5 from the proximal side, and a non-medical shoe may be readily worn over the foot-receiving portion 5. In other examples, toe end support and/or anterior support could be provided.

Examples of a material which may be used for one or both of the ankle-receiving portion 4 and the foot-receiving portion 5 are now described.

The material may comprise a first material and the ankle-receiving portion 4 and/or foot-receiving portion 5 may or may not comprise further material(s). The material may be polymeric, and may be 3D-printable.

The material may be rigid, at least relative to the resiliently deformable portion 3. The material may be configured not to substantially bend in dependence on ankle joint movement associated with walking.

In an example, the first material may comprise a polypropylene photopolymer such as Rigur™, marketed by Stratasys™. The first composition may have a tensile strength greater than 10 MPa according to the D-638-03 test. In a specific example, the tensile strength is from the range 40-45 MPa, for rigidity.

The material may optionally comprise a second, less rigid material. The second material may be polymeric, and may be 3D-printable. The second material may comprise a rubber-like photopolymer such as Agilus30 ™, marketed by Stratasys™. The second material may have a Shore A hardness less than 70. Its shore A hardness may be less than that of the first material. In a specific example, the Shore A hardness is from the range 20-40, or more specifically 30-35. Its tensile strength may be less than 10 MPa according to the ASTM D-412 test. In a specific example, its tensile strength may be from the range 2-4 MPa.

The second material may be blended with the first material in a controlled ratio. A greater proportion of the first material relative to the second increases the rigidity of the ankle-receiving portion 4 and the foot-receiving portion 5.

Other example polymeric materials for the first material and second material include thermoplastic elastomers and thermoplastic polymers. Example thermoplastic elastomers include thermoplastic polyurethanes, styrenic block copolymers, thermoplastic polyolefinelastomers, thermoplastic vulcanizates, thermoplastic copolyester, thermoplastic polyamides, etc. Example thermoplastic polymers include high-density polyethylene, acrylonitrile butadiene styrene, polyvinyl alcohol, polylactic acid, Polyethylene terephthalate, etc. Some non-polymeric materials are 3D-printable.

The relatively higher rigidity of the foot-receiving portion 5 and/or ankle-receiving portion 4 than the resiliently deformable portion 3 may be provided by one or more of: increasing elastic modulus; increasing shear modulus; increasing hardness; increasing second moment of area in one or more directions; or increasing torsion constant with respect to one or more axes.

In some examples, the ankle-receiving portion 4 and/or foot-receiving portion 5 may be reinforced. The reinforcement may comprise a further material more rigid than the first material, and/or different properties that are a function of their mesoscale geometry (e.g. lattice or mechanical metamaterial, rather than homogeneous material).

The reinforcement may protrude from a surrounding exterior surface of the ankle-receiving portion 4 and/or foot-receiving portion 5, or may be partially or fully embedded. Fully embedded reinforcement may be interior and therefore non-visible.

FIG. 1 further illustrates the ankle hinge 2 comprising the resiliently deformable portion 3.

The ankle hinge 2 is configured to control ankle movement in at least one direction by controlling movement of the ankle-receiving portion 4 relative to the foot-receiving portion 5.

With reference to FIG. 2, the at least one direction comprises dorsiflexion; plantarflexion; inversion; eversion; abduction; adduction; or a combination thereof. Control of dorsiflexion and plantarflexion is a particularly useful requirement for mobility.

The ankle hinge 2 may allow free unimpeded movement or no movement at all in selected directions other than the at least one direction to be controlled.

Figure 3A:
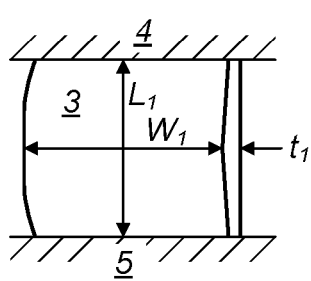
FIG. 3A illustrates a resiliently deformable portion in an un-deformed state and FIG. 3B illustrates the resiliently deformable portion in a deformed state.
Figure 3B:
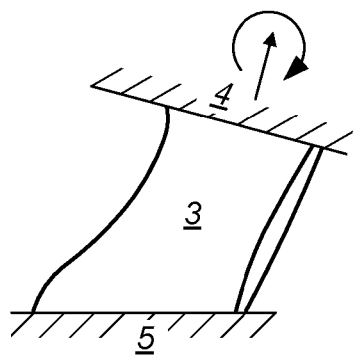

The ankle hinge 2 may couple the ankle-receiving portion 4 to the foot-receiving portion 5. FIGS. 3A and 3B illustrate that the resiliently deformable portion 3 has a length L1, a width W1 and a thickness t1 in its neutral equilibrium position (un-deformed). When deformed, the average length, width and thickness may differ in dependence on Poisson's ratio.

The resiliently deformable portion 3 is directly or indirectly coupled at one edge (e.g. lower edge) to the foot-receiving portion 5. The resiliently deformable portion 3 is directly or indirectly coupled at another edge (e.g. upper edge) to the ankle-receiving portion 4.

The resiliently deformable portion 3 is configured to resiliently deform in response to at least the ankle movement in the at least one direction to be controlled, to resist further ankle movement in the at least one direction. The resiliently deformable portion 3 may be configured to exhibit the deformation behaviour of an elastomer spring.

FIG. 3A shows the resiliently deformable portion 3 in its neutral equilibrium position. FIG. 3B shows the resiliently deformable portion 3 in a deformed state during dorsiflexion.

As the initial dorsiflexion rotates the foot-receiving portion 5 relative to the ankle-receiving portion 4, the resiliently deformable portion 3 is deformed from a neutral equilibrium position. This increases the restoring force of the resiliently deformable portion 3, to resist further ankle movement in the same direction.

In FIGS. 3A-3B, the upper and lower edges of the resiliently deformable portion 3 are rigid boundaries coupled to the ankle-receiving portion 4 and foot-receiving portions respectively. The rigid boundaries extend at least partially in the x-direction. The dorsiflexion may rotate the upper rigid boundary about the mediolateral axis and may also translate the upper rigid boundary away from the lower rigid boundary in the +z and/or +x directions. The differential movement results in differential contortion of the resiliently deformable portion 3. The dorsiflexion may cause a torsional load on the resiliently deformable portion 3.

The resiliently deformable portion 3 could be stiffer against tension and compression than against torsion, to resist ankle drop and inversion/eversion. Visco-elastic properties of the resiliently deformable portion 3 may be configured to dampen transfer of loads (such as walking loads) to a patient's body. For example, the resiliently deformable portion 3 may be configured not to oscillate or rebound beyond its neutral equilibrium un-deformed shape upon release of a walking-based deformation load.

The relative deformability of the resiliently deformable portion 3, compared to the rigid ankle/foot receiving portion, may be enabled by one or more of: reducing elastic modulus; reducing shear modulus; reducing hardness; reducing second moment of area in one or more directions; or reducing torsion constant with respect to one or more axes.

The resiliently deformable portion 3 comprises a first material which may be the same as the second material of the ankle/foot-receiving portions 4, 5, to provide elastomeric deformation properties. In some examples, the resiliently deformable portion 3 may additionally comprise a second material which may be the same as the first material of the ankle/foot-receiving portions 4, 5, to increase deformation resistance and durability.

For the resiliently deformable portion 3, the proportion of the second material used for the ankle/foot-receiving portions 4, 5 may be greater compared to the proportion used for the ankle/foot-receiving portions 4, 5. This means that the resiliently deformable portion 3 is more deformable than the ankle/foot-receiving portions 4, 5.

The overall shore A hardness of the resiliently deformable portion 3 composition may be less than 70 (ASTM D-2240), and in an example from the range 30-60. A Shore A hardness from the range 40-50 provides good deformability and robustness. Its tensile strength may be less than 5 MPa (ASTM D-412), and optionally from the range 2-4 MPa. Its elongation at break may be from the range 50% to 1000% (ASTM D-412), and optionally from the range 150-250%.

The resiliently deformable portion 3 may consist of a continuous isotropic homogeneous material. Optionally, the resiliently deformable portion 3 may comprise a mesoscale geometric structure. The structure may comprise a lattice or a mechanical metamaterial such as an auxetic, for example.

In other examples, the resiliently deformable portion 3 could be non-solid, such as a compressible fluid, in a sealed variable-volume cavity for compressing the fluid during use.

The at least one resiliently deformable portion 3 may be configured to support the weight of at least the ankle-receiving portion 4 such that a gap is maintained between the ankle-receiving portion 4 and the foot-receiving portion 5, at least while not worn by the patient. The ankle-receiving portion 4 may weigh 100 grams or more. The average gap between the ankle-receiving portion 4 and the foot-receiving portion 5 may be less than ten millimetres.

Referring to the dimensions of the resiliently deformable portion 3, the width W1 of the resiliently deformable portion 3 may be less than half of the maximum width of the ankle foot orthosis 1. The width may be from the range 1-5 cm depending on patient foot size. A greater width enables reduced thickness.

Reduced thickness makes for an easier fit of the ankle foot orthosis 1 inside a shoe, however strengthening may be required elsewhere. In an example, the average thickness t1 in the neutral equilibrium position is no more than approximately 8 mm, even no more than approximately 5 mm in some examples. This is less protruding than rivet-based hinges.

Referring now to the example of FIGS. 4A-4B, the ankle hinge 2 consists of two resiliently deformable portions 3 and no additional components. In other examples, the ankle hinge 2 may comprise fewer or additional resiliently deformable portions 3, and may comprise additional components other than resiliently deformable portions.

In FIGS. 4A-4B, lower edges of the resiliently deformable portions 3 are coupled to the lateral and medial side supports respectively, and may additionally be coupled to the posterior end support. The upper edges of the resiliently deformable portions 3 are coupled to a lower edge of the ankle-receiving portion 4. Therefore, the resiliently deformable portions 3 span the gap between the foot-receiving portion 5 and the ankle-receiving portion 4.

In other examples (not shown), the resiliently deformable portions 3 may be provided wholly at the foot-receiving portion 5 or wholly at the ankle-receiving portion 4, and indirectly couple to the other of the foot-receiving portion 5 or the ankle-receiving portion 4.

The resiliently deformable portions 3 are on the posterior side of the ankle foot orthosis 1, wherein the width (W1) of each resiliently deformable portion 3 extends in a posterior direction and towards the sagittal plane of the ankle foot orthosis 1. This shape of the lower edge of the resiliently deformable portion in the width direction (W1) follows the transition from the medial or lateral side support to the posterior end support. The transition may be a curve as shown in FIGS. 4A-4B, but could have another shape in other examples.

An advantage of locating the resiliently deformable portions 3 in the manner shown in FIGS. 4A-4B and described above, is that each resiliently deformable portion 3 can control movement in a plurality of directions. During dorsiflexion and plantarflexion, the resiliently deformable portions 3 are stretched and compressed to offer resistance. During inversion and eversion, one of the resiliently deformable portions 3 is compressed while the other encounters tension. During abduction and adduction, the resiliently deformable portions 3 twist.

In FIGS. 4A-4B, a space is provided between the resiliently deformable portions 3, behind the achilles tendon region (the most posterior point). Therefore, neither of the resiliently deformable portions 3 intersects the sagittal plane of the ankle foot orthosis 1.

The resiliently deformable portions 3 may protrude from the surrounding exterior surface of the ankle-receiving portion 4 and/or foot-receiving portion 5, as shown in FIGS. 4A-4B. The protrusion may be less than approximately 8 mm. The resiliently deformable portions 3 may not intrude into the cavity for the patient's foot.

As illustrated in FIGS. 4A-4B, one or more additional features other than the ankle hinge 2 may be provided to the ankle foot orthosis 1.

One such additional feature is means 9 for enabling the ankle-receiving portion 4 and/or the foot-receiving portion 5 to be secured to the human body. In FIGS. 4A-4B, the means comprises a portion for securing a strap. The portion may be provided on the ankle-receiving portion 4 as shown in FIGS. 4A-4B. The portion may be a loop or buckle, for example. The portion may comprise the same first material as the ankle-receiving portion 4, or a different material. The portion may enable a strap to be fastened and unfastened. In further examples, the strap is formed integrally with the rest of the ankle foot orthosis 1, and no loop or buckle is needed.

Another additional feature is an insole layer 6 for providing cushioning to a patient's foot. In FIGS. 4A-4B, the insole layer 6 may be located on at least part of the foot-receiving portion 5, between the patient's foot and the foot-receiving portion 5. The insole layer 6 may comprise the same first material as the foot-receiving portion 5, or a different material such as a woven textile if not 3D printed. The insole layer 6 could be made less hard and/or more deformable than the foot-receiving portion 5. The insole layer 6 could comprise a mechanical metamaterial such as auxetic or pentamode, for effective cushioning.

If the ankle foot orthosis 1 is not made to a patient's specific body shape, the insole layer 6 could be shaped to adapt the ankle foot orthosis 1 to the patient's body shape.

Another additional feature is an inner layer 7 on at least a portion of the ankle-receiving portion 4. The inner layer 7 shown in FIGS. 4A-4B may comprise the same material as the insole layer 6. The inner layer 7 may be between the ankle-receiving portion 4 and the patient's ankle.

Another additional feature is one or more apertures 8 for enabling air circulation to a patient's skin. In FIGS. 4A-4B, the apertures 8 are provided on the ankle-receiving portion 4. However, apertures 8 could be provided on the foot-receiving portion 5 in some examples.

In FIGS. 4A-4B, a plurality of the apertures 8 is provided. There are more than ten or more than a hundred apertures 8. The apertures 8 could be distributed across the whole ankle-receiving portion 4, or in a localized area as shown in FIGS. 4A-4B. The localized area illustrated is in the posterior region in the centre of the ankle-receiving portion 4, where continuous contact with the patient's calf may occur.

Another additional feature is a toe hinge 10 for enabling toe flexion. In FIGS. 4A-4B, the toe hinge 10 is a feature of the foot-receiving portion 5. The toe hinge 10 may comprise one or more portions 11 of reduced material thickness (toe portions' herein) for enabling the toe flexion, as illustrated. However, other toe hinges could be provided in other examples to achieve a similar effect. An advantage of the toe hinge 10 shown in FIGS. 4A-4B is ease of manufacture, particularly additive manufacture.

Figure 5:
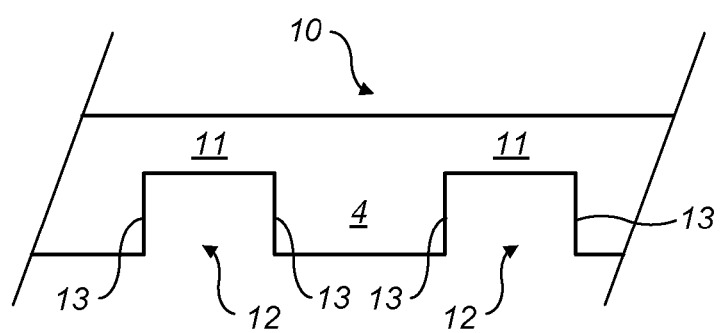
FIG. 5 illustrates an example of a toe hinge.

The toe portions 11 may be formed by channels 12, depths of the channels 12 defining the extent of the reduced material thickness of the sole. FIGS. 4A-4B show channels 12 and FIG. 5 shows a detail view of the channels 12. The channels 12 may extend between medial and lateral sides of the foot-receiving portion 5. Neighbouring channels 12 may be spaced along the x-axis (anterior-posterior axis).

The channels 12 may be empty of material, or may be filled with a more deformable material than the foot-receiving portion 5. The illustrated toe hinge 10 comprises a plurality of channels 12. More than five channels 12 are visible in the illustrations.

The illustrated channels 12 comprise walls 13. The channels 12 may comprise a floor or may be V-shaped in cross-section, or have another cross-section shape.

The illustrated channels 12 are open to the underside of the sole of the foot-receiving portion 5. In other examples, the channels 12 may be open to the top surface of the foot-receiving portion 5 facing a patient's foot, or a mix of both channel orientations could be provided. The channels 12 could even be closed channels 12 and therefore in the interior of the foot-receiving portion 5.

The channel depths may vary, as shown in FIGS. 4A-4B. For instance, a first and/or last channel 12 in a series of channels 12 may be less deep than one or more middle channels 12 in the series. This reduces stress concentrations. The channel depths may be constant or may vary along the lengths of the channels 12 between the medial and lateral sides of the foot-receiving portion 5.

As shown in FIG. 5, the channels 12 may be dimensioned such that facing channel walls 13 of the channels 12 abut during toe flexion to inhibit further toe flexion. A channel 12 may be narrow along at least a portion of its length. Facing walls 13 of the channel 12 will move closer together during toe clenching (toe plantarflexion), until the walls 13 abut to inhibit further plantarflexion. No such resistance is offered against toe dorsiflexion in the illustrations, although toe dorsiflexion inhibitors may be provided in other examples, for instance using narrow channels 12 open at the top surface of the foot-receiving portion 5.

Regarding the method of manufacture of an ankle foot orthosis 1 as discussed herein, additive manufacture could be used. In other examples, the ankle foot orthosis 1 could be moulded or fabricated. However, additive manufacturing is desirable for making ankle foot orthoses that are customized for each patient. A 3D printer controller can be provided with information derived from patient scan data, enabling a well-fitting ankle foot orthosis 1 to be made.

To simplify the manufacture, multiple components disclosed herein could comprise at least one material in common. For example, the components may be printed in a first configuration (e.g. simulating elastomer properties) to form the resiliently deformable portion(s) 3, and may be printed in a second configuration to form the rigid foot/ankle-receiving portions 4, 5. The first configuration may be a first ratio of the first and second materials, and the second configuration may be a second ratio of the first and second materials. The ratio may be changed during printing to control rigidity and deformability without a need for human intervention or movement of the orthosis. For example, the first and second materials may be filaments on reels, drawn at an automatically controlled rate. Therefore, there is no need to change materials or attempt to attach dissimilar materials together.

Further, the foot-receiving portion 5, ankle-receiving portion 4 and ankle hinge 2 could be printed in a single stage (step) print, so that separate assembly (e.g. by a human) is not required. The single stage print could also form the insole layer 6, the inner layer 7, the toe hinge 10, the apertures 8, the means for enabling the ankle-receiving portion 4 and/or the foot-receiving portion 5 to be secured to the human body, or a combination thereof. Little to no post-printing fabrication is therefore required.

Although embodiments of the present invention have been described in the preceding paragraphs with reference to various examples, it should be appreciated that modifications to the examples given can be made without departing from the scope of the invention as claimed. For example, instead of a resiliently deformable portion 3, another means may be provided for progressively resisting further ankle movement in at least the first direction as the ankle movement increases in the first direction. Examples could rely on varying friction, hydraulic devices, electromagnetic devices, or pneumatic devices.

Further, the resiliently deformable portion could be advantageously applied to hinges of other orthoses than an ankle foot orthosis.

Features described in the preceding description may be used in combinations other than the combinations explicitly described.

Although functions have been described with reference to certain features, those functions may be performable by other features whether described or not.

Although features have been described with reference to certain embodiments, those features may also be present in other embodiments whether described or not.

Whilst endeavoring in the foregoing specification to draw attention to those features of the invention believed to be of particular importance it should be understood that the Applicant claims protection in respect of any patentable feature or combination of features hereinbefore referred to and/or shown in the drawings whether or not particular emphasis has been placed thereon.

We claim:

1. A method of manufacturing an ankle foot orthosis configured to control joint motion, the method comprising:
    providing the ankle foot orthosis, the ankle foot orthosis comprising an ankle hinge configured to control ankle movement in at least one direction;
    wherein the ankle hinge comprises at least one resiliently deformable portion, and wherein the resiliently deformable portion is configured to resiliently deform in response to at least the ankle movement in the at least one direction, to resist further ankle movement in the at least one direction,
    wherein at least part of the ankle foot orthosis is 3D printed based on scanned patient data,
    wherein the resiliently deformable portion is on a heel side of the ankle foot orthosis, and a width of the resiliently deformable portion extends in a posterior direction to a posterior end region while curving towards a sagittal plane of the ankle foot orthosis, wherein the resiliently deformable portion has an average thickness of no more than approximately 8 mm.

2. The method of claim 1, wherein the ankle hinge enables movement of an ankle-receiving portion relative to a foot-receiving portion, wherein the ankle-receiving portion and the foot-receiving portion are rigid relative to the resiliently deformable portion.

3. The method of claim 2, wherein a lengthwise direction of the resiliently deformable portion spans from the foot-receiving portion to the ankle-receiving portion.

4. The method of claim 2, wherein the at least one resiliently deformable portion is configured to support the weight of at least the ankle-receiving portion such that a gap is maintained between the ankle-receiving portion and the foot-receiving portion.

5. The method of claim 2, wherein the resiliently deformable portion comprises a first material, and wherein at least one of the foot-receiving portion or the ankle-receiving portion comprises the same first material.

6. The method of claim 1, comprising a toe hinge configured to enable toe flexion.

7. The method of claim 6, wherein the toe hinge comprises a plurality of portions of reduced material thickness to enable the toe flexion.

8. The method of claim 7, wherein the one or more portions are provided by channels, depths of the channels defining the extent of the reduced material thickness, wherein the channels are dimensioned such that facing channel walls of the channels abut during toe flexion in a first toe flexion direction to inhibit further toe flexion in the first toe flexion direction.

9. The method of claim 1, wherein providing the ankle foot orthosis comprises:
    providing an ankle-receiving portion and a foot-receiving portion, wherein the ankle-receiving portion and the foot-receiving portion are rigid relative to the resiliently deformable portion.

10. The method of claim 9, wherein at least one of the resiliently deformable portion, the ankle-receiving portion, or the foot-receiving portion, and another of the resiliently deformable portion, the ankle-receiving portion, or the foot-receiving portion, are formed by a single step 3D print.

11. The method of claim 1, wherein the at least one direction comprises dorsiflexion or plantarflexion, wherein the resiliently deformable portion is configured to resiliently stretch in response to the dorsiflexion or plantarflexion.

12. The method of claim 1, wherein the at least one direction comprises a plurality of directions, the plurality of directions selected from the group comprising: dorsiflexion; plantarflexion; inversion; eversion; abduction; or adduction.

13. The method of claim 1, wherein the resiliently deformable portion comprises material with a shore A hardness of less than 70.

14. The method of claim 1, wherein the width of the resiliently deformable portion is less than half of a maximum width of the ankle foot orthosis.

15. The method of claim 1, wherein the resiliently deformable portion is a first resiliently deformable portion on one of a medial or lateral side of the ankle foot orthosis, the ankle hinge further comprising a second resiliently deformable portion on the other of the medial or lateral side.

16. The method of claim 1, comprising a group of more than ten apertures configured to enable air circulation to a patient's skin.

17. A method of manufacturing an ankle foot orthosis configured to control joint motion, the method comprising:
    providing the ankle foot orthosis, the ankle foot orthosis comprising an ankle hinge configured to control ankle movement in at least one direction;
    wherein the ankle hinge comprises at least one resiliently deformable portion, and wherein the resiliently deformable portion is configured to resiliently deform in response to at least the ankle movement in the at least one direction, to resist further ankle movement in the at least one direction,
    wherein at least part of the ankle foot orthosis is 3D printed based on scanned patient data,
    wherein the ankle foot orthosis comprises a toe hinge configured to enable toe flexion, the toe hinge comprises a plurality of portions of reduced material thickness to enable the toe flexion.

18. The method of claim 17, wherein the one or more portions are provided by channels, depths of the channels defining the extent of the reduced material thickness, wherein the channels are dimensioned such that facing channel walls of the channels abut during toe flexion in a first toe flexion direction to inhibit further toe flexion in the first toe flexion direction.

19. The method of claim 17, wherein the resiliently deformable portion has an average thickness of no more than approximately 8 mm.

20. An ankle foot orthosis configured to control joint movement, the ankle foot orthosis comprising:
    an ankle hinge configured to control ankle movement in at least one direction;
    wherein the ankle hinge comprises at least one resiliently deformable portion, and wherein the resiliently deformable portion is configured to resiliently deform in response to at least the ankle movement in the at least one direction, to resist further ankle movement in the at least one direction,
    wherein at least part of the ankle foot orthosis is a 3D printed part based on scanned patient data,
    wherein the resiliently deformable portion is on a heel side of the ankle foot orthosis, and a width of the resiliently deformable portion extends in a posterior direction to a posterior end region while curving towards a sagittal plane of the ankle foot orthosis, wherein the resiliently deformable portion has an average thickness of no more than approximately 8 mm.

* * * * *